US011168342B2

(12) United States Patent
Wichelecki et al.

(10) Patent No.: US 11,168,342 B2
(45) Date of Patent: *Nov. 9, 2021

(54) ENZYMATIC PRODUCTION OF D-ALLULOSE

(71) Applicant: BONUMOSE, INC., Charlottesville, VA (US)

(72) Inventors: Daniel Joseph Wichelecki, Charlottesville, VA (US); Edwin O. Rogers, Charlottesville, VA (US)

(73) Assignee: BONUMOSE, INC., Charlottesville, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/112,033

(22) Filed: Dec. 4, 2020

(65) Prior Publication Data

US 2021/0108241 A1   Apr. 15, 2021

Related U.S. Application Data

(60) Continuation of application No. 16/818,107, filed on Mar. 13, 2020, now Pat. No. 11,053,528, which is a division of application No. 16/468,916, filed as application No. PCT/US2017/066298 on Dec. 14, 2017, now Pat. No. 11,078,506.

(60) Provisional application No. 62/434,033, filed on Dec. 14, 2016.

(51) Int. Cl.
| | |
|---|---|
| *C12P 19/24* | (2006.01) |
| *C12P 19/04* | (2006.01) |
| *C12P 19/02* | (2006.01) |
| *C12N 9/16* | (2006.01) |
| *C12N 9/90* | (2006.01) |
| *C07H 3/02* | (2006.01) |
| *C07H 1/00* | (2006.01) |
| *C12N 9/10* | (2006.01) |

(52) U.S. Cl.
CPC ............. *C12P 19/24* (2013.01); *C07H 1/00* (2013.01); *C07H 3/02* (2013.01); *C12N 9/1051* (2013.01); *C12N 9/16* (2013.01); *C12N 9/90* (2013.01); *C12P 19/02* (2013.01); *C12Y 204/01001* (2013.01); *C12Y 204/01007* (2013.01); *C12Y 204/01008* (2013.01); *C12Y 501/03* (2013.01); *C12Y 501/03001* (2013.01); *C12Y 503/01009* (2013.01); *C12Y 504/02002* (2013.01); *C12P 2203/00* (2013.01); *C12Y 503/02002* (2013.01)

(58) Field of Classification Search
CPC .......... C12N 9/90; C12N 9/1051; C12N 9/92; C12N 9/2431; C12P 19/02; C12P 19/24; C12Y 503/01009; C12Y 204/01001; C12Y 204/01007; C12Y 301/03011; C12Y 302/01026

USPC ............................. 435/155, 189, 190, 252.3
See application file for complete search history.

(56) References Cited

U.S. PATENT DOCUMENTS

| | | |
|---|---|---|
| 10,316,342 B2 | 6/2019 | Maceachran et al. |
| 2005/0042734 A1 | 2/2005 | Bao et al. |
| 2015/0210996 A1 | 7/2015 | Woodyer et al. |
| 2015/0284759 A1 | 10/2015 | Gullapalli et al. |
| 2016/0168275 A1 | 6/2016 | Santanocito et al. |
| 2018/0320210 A1 | 11/2018 | Maceachran et al. |

FOREIGN PATENT DOCUMENTS

| | | |
|---|---|---|
| EP | 2990483 A1 | 3/2016 |
| EP | 3480306 A2 | 5/2019 |
| KR | 20050065547 A | 6/2005 |
| WO | 2011/040708 A2 | 4/2011 |
| WO | 2014/049373 A1 | 4/2014 |
| WO | 2015/032761 A1 | 3/2015 |
| WO | 2018/004308 A2 | 4/2018 |
| WO | 2018/129275 A1 | 7/2018 |

OTHER PUBLICATIONS

Proteins: Structure, Function and Genetics, 2000, vol. 41: 98-107.*
Whisstock et al., (Quarterly Reviews of Biophysics 2003, vol. 36 (3): 307-340.*
Witkowski et al., (Biochemistry 38:11643-11650, 1999.*
Kisselev L., (Structure, 2002, vol. 10: 8-9.*
International Search Report and Written Opinion in International Application No. PCT/US2017/066298, dated Apr. 9, 2018.
Chan et al., Biochemistry, Sep. 9, 2008; 47(36): 9608-9617.
Third Party Observation filed in International Application No. PCT/US2017/0066298, filed on Jan. 25, 2019.
Willem et al., Biochem. J. (1990) 265, 519-521.
Zhou et al., J. Agric. Food Chem., pp. A-G.
Huang et al., PNAS, Apr. 6, 2015, pp. E1974-E1983.
Kim et al., J. Biological Chemistry, vol. 279, No. 1, 2004, pp. 517-526.
London et al., Supporting Information, ACS Publications, Biochemistry, 2015, 54 pp. 528-537.
Annual Meeting Minutes of the Japan Society for Bioscience, Biotechnology and Agrochemistry, 2016.
Morais et al., Biochemistry, 2000, 39, pp. 10385-10396.
Yamamoto et al., Acta Cryst. 2008, D64. pp. 1068-1077.
Additional comments to Third Party Observation filed in International Application No. PCT/US2017/0066298, filed on Jan. 25, 2019.
Masuda et al., Journal of Biological Chemistry, vol. 276, No. 41, 2001, pp. 37794-37801.

(Continued)

*Primary Examiner* — Robert B Mondesi
*Assistant Examiner* — Mohammad Y Meah
(74) *Attorney, Agent, or Firm* — J.A. Lindeman & Co., PLLC

(57) ABSTRACT

The current disclosure provides a process for enzymatically converting a saccharide into allulose. The invention also relates to a process for preparing allulose where the process involves converting fructose 6-phosphate (F6P) to allulose 6-phosphate (A6P), catalyzed by allulose 6-phosphate 3-epimerase (A6PE), and converting the A6P to allulose, catalyzed by allulose 6-phosphate phosphatase (A6PP).

8 Claims, 7 Drawing Sheets

Specification includes a Sequence Listing.

(56) References Cited

OTHER PUBLICATIONS

NBCI (2019 updated) "ribulose-phospharte 3-epimerase [Clostridioides difficile 630]", pp. 1-3.
Brenda (2019 update) enzymes having EC 5.1.3.-. pp. 1-3.
Devos et al., (Proteins: Structure, Function and Genetics, 2000, vol. 41: 98-107.
Chan et al. Biochem 2008, 4 7 pp. 9608-9617.
Schinzel et al FEMS microbial let. 1999, 171, pp. 73-79.
Ma etal. Biochem. 1980, 19, pp. 751-759.
Willem et al. J. Biol Chem. 1992, 267, pp. 210-217.
Allen and Dunaway-Mariano: Evolution of New Specificities in a Superfamily of Phosphatases. Experimental Standard Conditions of Enzyme Characterizations. pp. 67-77. (Sep. 14, 2010).
Lu et al. HAD Superfamily Phosphotransferase Substrate Diversification: Structure and Function Analysis of HAO Subclass IIB Sugar Phosphatase BT4131. Biochemistry. 44(24): 8684-8696. (Jun. 1, 2005).
Geneseq. Sequence "*Escherichia coli* str. K-12 substr. MG1655 alsE protein, Seq ID 15". XP002799356, retrieved from EBI accession No. GSP: AZK99160 Database accession No. AZK99160. (Sep. 15, 2011). Y KR 2011 041 910 A (Univ Gyeongsang Indacad Coop Found), (Apr. 22, 2011).
UniProt Sequence Q89ZR1. HPr (Ser) phosphatase. Bacteroides thetaiotaomicron (strain ATCC 29148/DSM 2079/NCTC 10582/E50/VPI-5482). URL: https://www.uniprot.org/uniprot/Q89ZR1. (Jun. 1, 2003).

\* cited by examiner

SEQUENCE LISTING

```
<160> NUMBER OF SEQ ID NOS: 9

<210> SEQ ID NO 1
<211> LENGTH: 663
<212> TYPE: DNA
<213> ORGANISM: Thermoanaerobacterium thermosaccharolyticum

<400> SEQUENCE: 1
atgaaatatt tattttcgcc atctttaatg tgtatgaatt taatcaagct aaatgaacaa      60
atatctgttc ttaatagcaa ggcggatttt ttgcatgttg acatcatgga tggccatttt     120
gttaaaaata ttactttatc accgtttttt atagagcaga ttaaatcata tgtcaatatt     180
cctattgatg cacaccttat ggtagaaaat ccaggtgatt atattgaaat atgcgaaaaa     240
tcgggagcaa gttttataac tatacatgca gaaacaatta atagagaagc atttagaata     300
atagatagaa ttaaaagtca tggactcatg gttggcatag cattgaatcc agcaacacct     360
atttcggaaa ttaaacatta tattaataaa atagataaga taacaataat gactgtcgat     420
cccggcttcg ctggtcaacc atttattccg gaggtattgg aaaagatccg agatctaaag     480
agactgaaag atgataataa ttataattat ttaattgaag cagatggttc ctgcaataaa     540
aatacgtttc aagtgctaaa agatgccgga tgtaaagttt tcgtattagg ttcatcaggg     600 cttttttaatc ttagcgatga tttgggaaaa gcgtgggaaa taatgattgg caattttaat     660
gga                                                                  663

<210> SEQ ID NO 2
<211> LENGTH: 663
<212> TYPE: DNA
<213> ORGANISM: Artificial Sequence
<220> FEATURE:
<223> OTHER INFORMATION: Codon optimized thermoanaerobacterium
      thermosaccharolyticum A6PE

<400> SEQUENCE: 2
atgaagtacc tgtttagccc gagcctgatg tgcatgaatc tgattaagct gaatgaacag      60
attagcgttc tgaatagcaa agccgatttt ctgcatgttg atattatgga tggtcatttt     120
gttaagaaca tcaccctgag ccgttttc attgaacaga ttaagagcta tgtgaatatc     180
ccgattgatg cccatctgat ggtggaaaat ccgggtgact atattgaaat ttgtgaaaaa     240 agcgcgcaa gttttattac cattcatgcc gaaaccatta tcgtgaagc atttcgtatt     300 attgaccgta ttaagagtca tggtctgatg gtgggcattg cactgaatcc ggccaccccg     360
attagcgaaa ttaagcatta tattaacaag atcgacaaga tcaccattat gaccgttgat     420
```

```
ccgggctttg caggccagcc gtttattccg gaagtgctgg aaaaaattcg cgatctgaaa      480
cgtctgaaag atgataataa ttacaactac ctgatcgaag ccgatggtag ttgcaataag      540 aataccttc aggttctgaa agatgcaggc tgcaaagttt ttgtgctggg cagtagcggt       600
ctgtttaatc tgagtgatga tctgggcaaa gcatgggaaa ttatgattgg caattttaat     660
ggc                                                                    663
```

<210> SEQ ID NO 3
<211> LENGTH: 221
<212> TYPE: PRT
<213> ORGANISM: Thermoanaerobacterium thermosaccharolyticum

<400> SEQUENCE: 3

```
Met Lys Tyr Leu Phe Ser Pro Ser Leu Met Cys Met Asn Leu Ile Lys
1               5                   10                  15

Leu Asn Glu Gln Ile Ser Val Leu Asn Ser Lys Ala Asp Phe Leu His
            20                  25                  30

Val Asp Ile Met Asp Gly His Phe Val Lys Asn Ile Thr Leu Ser Pro
        35                  40                  45

Phe Phe Ile Glu Gln Ile Lys Ser Tyr Val Asn Ile Pro Ile Asp Ala
    50                  55                  60

His Leu Met Val Glu Asn Pro Gly Asp Tyr Ile Glu Ile Cys Glu Lys
65                  70                  75                  80

Ser Gly Ala Ser Phe Ile Thr Ile His Ala Glu Thr Ile Asn Arg Glu
                85                  90                  95

Ala Phe Arg Ile Ile Asp Arg Ile Lys Ser His Gly Leu Met Val Gly
            100                 105                 110

Ile Ala Leu Asn Pro Ala Thr Pro Ile Ser Glu Ile Lys His Tyr Ile
        115                 120                 125

Asn Lys Ile Asp Lys Ile Thr Ile Met Thr Val Asp Pro Gly Phe Ala
    130                 135                 140

Gly Gln Pro Phe Ile Pro Glu Val Leu Glu Lys Ile Arg Asp Leu Lys
145                 150                 155                 160

Arg Leu Lys Asp Asp Asn Asn Tyr Asn Tyr Leu Ile Glu Ala Asp Gly
                165                 170                 175

Ser Cys Asn Lys Asn Thr Phe Gln Val Leu Lys Asp Ala Gly Cys Lys
            180                 185                 190

Val Phe Val Leu Gly Ser Ser Gly Leu Phe Asn Leu Ser Asp Asp Leu
        195                 200                 205

Gly Lys Ala Trp Glu Ile Met Ile Gly Asn Phe Asn Gly
    210                 215                 220
```

<210> SEQ ID NO 4
<211> LENGTH: 690
<212> TYPE: DNA
<213> ORGANISM: Bacillus thermoamylovorans

<400> SEQUENCE: 4

```
atgagcaaca aaattgaatt ttcaccgtct ttaatgacaa tggatttaga caagtttaaa      60
gaacagatta cttttttaaa taatcatgtc ggttcttacc atatcgatat tatggacgga     120
cattatgtac ctaatataac tctatcccct tggtttgtcc aagaggtacg gaaaattagt     180
gatgttccga tgtctgccca cttgatggtc acaaacccaa gttttgggt acaacaactc      240 attgatatta gtgtgaatg gatttgcatg cacgtagaaa cccttgatgg gttagctttc      300
```

```
cgcttaattg atcaaatcca cgatgcggga ttaaaagcag gggtcgtatt aaatcctgaa    360
acaagtgttg atgcgattcg cccgtacatt gatttagtgg ataaagtcac cattatgact    420
gtcgacccag gttttgcagg tcaacgcttt attgatagta cattggagaa atcgtggaa     480 ttaagaaaat tacgggaaga cacggttat aaatatgtga ttgaaatgga tggatcttcg     540
aatcggaaat ccttcaagaa aatttatgaa gccggtcctg acatttatat tataggtcgc    600
agcggtttgt ttggattaca cgaagatatc gaaaaagcat gggaaatcat gtgcaaagat    660
tttgaggaaa tgactggcga aaaagtatta                                     690
```

<210> SEQ ID NO 5
<211> LENGTH: 690
<212> TYPE: DNA
<213> ORGANISM: Artificial Sequence
<220> FEATURE:
<223> OTHER INFORMATION: Thermophilic A6PE from Bacillus
    thermoamylovorans Codon optimized <400> SEQUENCE: 5

```
atgagtaaca agatcgaatt cagcccgagc ctgatgacca tggatctgga taaatttaaa    60
gaacagatca ccttttctgaa caatcatgtt ggcagttatc atattgatat catggatggt    120
cattacgtgc cgaatattac cctgagcccg tggtttgttc aggaagtgcg caaaattagc    180
gatgttccga tgagcgcaca tctgatggtt accaatccga gttttgggt tcagcagctg     240 attgatatta atgtgaatg atttgcatg catgttgaaa ccctggatgg cctggccttt     300
cgtctgattg atcagattca tgatgccggc ctgaaagcag gtgtggttct gaatccggaa    360
accagtgtgg atgccattcg tccgtatatt gatctggttg ataaagttac catcatgacc    420
gtggatccgg cttttgccgg ccagcgcttt attgatagca ccctggaaaa aattgtggaa    480
ctgcgtaaac tgcgtgaaga acatggttat aaatatgtga ttgagatgga tggcagcagc    540
aatcgcaaaa gctttaaaaa aatttacgag gcaggtccgg atatttatat tattggccgt    600
agtggcctgt ttggcctgca tgaagatatt gaaaaagcat gggaaattat gtgtaaggat    660
tttgaagaaa tgaccggtga aaaagtgctg                                     690
```

<210> SEQ ID NO 6
<211> LENGTH: 230
<212> TYPE: PRT
<213> ORGANISM: Bacillus thermoamylovorans
<400> SEQUENCE: 6

```
Met Ser Asn Lys Ile Glu Phe Ser Pro Ser Leu Met Thr Met Asp Leu
1               5                   10                  15

Asp Lys Phe Lys Glu Gln Ile Thr Phe Leu Asn Asn His Val Gly Ser
            20                  25                  30

Tyr His Ile Asp Ile Met Asp Gly His Tyr Val Pro Asn Ile Thr Leu
        35                  40                  45

Ser Pro Trp Phe Val Gln Glu Val Arg Lys Ile Ser Asp Val Pro Met
    50                  55                  60

Ser Ala His Leu Met Val Thr Asn Pro Ser Phe Trp Val Gln Gln Leu
65                  70                  75                  80

Ile Asp Ile Lys Cys Glu Trp Ile Cys Met His Val Glu Thr Leu Asp
                85                  90                  95

Gly Leu Ala Phe Arg Leu Ile Asp Gln Ile His Asp Ala Gly Leu Lys
            100                 105                 110

Ala Gly Val Val Leu Asn Pro Glu Thr Ser Val Asp Ala Ile Arg Pro
```

Tyr Ile Asp Leu Val Asp Lys Val Thr Ile Met Thr Val Asp Pro Gly
        115                 120                 125
Phe Ala Gly Gln Arg Phe Ile Asp Ser Thr Leu Glu Lys Ile Val Glu
145                 150                 155                 160

Leu Arg Lys Leu Arg Glu Glu His Gly Tyr Lys Tyr Val Ile Glu Met
            165                 170                 175

Asp Gly Ser Ser Asn Arg Lys Ser Phe Lys Lys Ile Tyr Glu Ala Gly
                180                 185                 190

Pro Asp Ile Tyr Ile Ile Gly Arg Ser Gly Leu Phe Gly Leu His Glu
            195                 200                 205

Asp Ile Glu Lys Ala Trp Glu Ile Met Cys Lys Asp Phe Glu Glu Met
210                 215                 220

Thr Gly Glu Lys Val Leu
225                 230

<210> SEQ ID NO 7
<211> LENGTH: 651
<212> TYPE: DNA
<213> ORGANISM: Clostridium thermocellum

<400> SEQUENCE: 7

```
atgattaaat acaaagcggt attctttgat tttgactata cgctggcaga ttcatctaaa      60
gctgttatag aatgtattaa ctatgcactg caaaaaatgg ttatcccga atcttctccg      120 gaaagtattt gcagaacaat aggacttacg ttggccgagg cttttaaaat acttagcggg     180
gatacttctg attccaatgc ggaccttttc cgccaatact taaagaaag agcagatctg      240 gttatgtgtg accggactgt aatgtacagc actgttgaat gtgttttgaa gaagctgaaa    300
aaggcggatg taaaaacagg aattgtttca acgaagtaca gatacaggat agaggatata    360
ttaaaaaggg acaaactttt acagtatttt gatgtaattg tcggcgggga agatgttgcg    420
gcccataaac cggatccgga agggcttcta aaggccatat cgatggttgg ctgccaaaag    480
gaagaagtcc tttttgtcgg agacagtacg gtggatgcaa ggactgcaaa aaatgcggga    540
gtggattttg tggcggttct tacggggaca accggggcaa atgagttttc agagtataat    600
cctggtgctg tgattgaaga tttgagtggt ttattggata tgtttatgtt a             651
```

<210> SEQ ID NO 8
<211> LENGTH: 651
<212> TYPE: DNA
<213> ORGANISM: Artificial Sequence
<220> FEATURE:
<223> OTHER INFORMATION: Codon optimized A6PP from Clostridium
      thermocellum

<400> SEQUENCE: 8

```
atgatcaagt acaaggccgt ttttttgat tttgattaca ccctggcaga tagcagcaaa      60
gccgttattg aatgtattaa ttacgccctg cagaaaatgg ctatcccgga aagcagtccg    120
gaaagcattt gtcgtaccat tggcctgacc ctggcagaag catttaaaat tctgagcggt    180
gataccagcg atagcaatgc cgatctgttt cgccagtatt taaagaacg cgcagatctg    240 gttatgtgtg atcgcaccgt gatgtatagc accgtgaat gcgtgctgaa aaaactgaaa    300
aaagcagatg ttaagaccgg tattgtgagc accaaatatc gctatcgtat tgaagatatt    360
ctgaaacgtg ataaactgct gcagtatttt gatgttattg ttggtggcga agatgttgcc    420
gcccataaac cggatccgga aggcctgctg aaagcaatta gcatggtggg ctgccagaaa    480
```

```
gaagaagttc tgtttgttgg tgatagcacc gttgatgcac gtaccgccaa aaatgcaggc    540
gtggattttg tggccgttct gaccggcacc accggcgcaa atgaatttag cgaatataat    600
ccgggcgccg tgattgaaga tctgagcggt ctgctggata tgtttatgct g            651

<210> SEQ ID NO 9
<211> LENGTH: 217
<212> TYPE: PRT
<213> ORGANISM: Clostridium thermocellum

<400> SEQUENCE: 9

Met Ile Lys Tyr Lys Ala Val Phe Phe Asp Phe Asp Tyr Thr Leu Ala
1               5                   10                  15

Asp Ser Ser Lys Ala Val Ile Glu Cys Ile Asn Tyr Ala Leu Gln Lys
            20                  25                  30

Met Gly Tyr Pro Glu Ser Ser Pro Glu Ser Ile Cys Arg Thr Ile Gly
        35                  40                  45

Leu Thr Leu Ala Glu Ala Phe Lys Ile Leu Ser Gly Asp Thr Ser Asp
    50                  55                  60

Ser Asn Ala Asp Leu Phe Arg Gln Tyr Phe Lys Glu Arg Ala Asp Leu
65                  70                  75                  80

Val Met Cys Asp Arg Thr Val Met Tyr Ser Thr Val Glu Cys Val Leu
                85                  90                  95

Lys Lys Leu Lys Lys Ala Asp Val Lys Thr Gly Ile Val Ser Thr Lys
            100                 105                 110

Tyr Arg Tyr Arg Ile Glu Asp Ile Leu Lys Arg Asp Lys Leu Leu Gln
        115                 120                 125

Tyr Phe Asp Val Ile Val Gly Gly Glu Asp Val Ala Ala His Lys Pro
    130                 135                 140

Asp Pro Glu Gly Leu Leu Lys Ala Ile Ser Met Val Gly Cys Gln Lys
145                 150                 155                 160

Glu Glu Val Leu Phe Val Gly Asp Ser Thr Val Asp Ala Arg Thr Ala
                165                 170                 175

Lys Asn Ala Gly Val Asp Phe Val Ala Val Leu Thr Gly Thr Thr Gly
            180                 185                 190

Ala Asn Glu Phe Ser Glu Tyr Asn Pro Gly Ala Val Ile Glu Asp Leu
        195                 200                 205

Ser Gly Leu Leu Asp Met Phe Met Leu
    210                 215
```

ENZYMATIC PRODUCTION OF D-ALLULOSE

CROSS-REFERENCE TO RELATED APPLICATIONS

This application is a continuation application of U.S. application Ser. No. 16/818,107, filed on Mar. 13, 2020, U.S. Pat. No. 11,053,528, which is divisional application of U.S. application Ser. No. 16/468,916, filed on Jun. 12, 2019, U.S. Pat. No. 11,078,506, which is a 371 application of International Application No. PCT/US/2017/066298, filed on Jun. 14, 2017, which claims priority to U.S. Application No. 62/434,033, filed on Dec. 14, 2016, which is incorporated herein by reference.

SEQUENCE LISTING

The Sequence Listing submitted herewith is an ASCII text file (2020-12-04_Sequence Listing.text, created on Dec. 4, 2020, 16384 bytes) via EFS-Web is hereby incorporated by reference.

FIELD OF THE INVENTION

The invention relates to preparation of the sugar D-allulose. More specifically, the invention relates to methods of preparing D-allulose by enzymatically converting saccharides (e.g., polysaccharides, oligosaccharides, disaccharides, sucrose, D-glucose, and D-fructose) into D-allulose.

BACKGROUND OF THE INVENTION

D-allulose (also known as D-psicose) (allulose hereafter) is a low-calorie, natural sweetener that has 70% the sweetness of sucrose, but only 10% of the calories. It is a naturally occurring monosaccharide hexose that is present in only small amounts in wheat and other plants. Allulose was approved as a food additive by the Food and Drug Administration (FDA) in 2012, which designated it as generally recognized as safe (GRAS). However, due to allulose's high selling prices, its use as a sweetener has been limited. Allulose boasts a myriad of health benefits: it is low-calorie (10% of sucrose); it has a very low glycemic index of 1; it is fully absorbed in the small intestine but not metabolized and instead secreted in urine and feces; it helps regulate blood sugar by inhibiting alpha-amylase, sucrase and maltase; and it has similar functionality in foods and beverages as sucrose. As such, allulose clearly has a variety of applications in the food and beverage industries.

Currently allulose is produced predominantly through the enzymatic isomerization of fructose (WO 2014049373). Overall, the method suffers because of higher feedstock cost, the costly separation of allulose from fructose, and relatively low product yields.

There is a need to develop a cost-effective synthetic pathway for high-yield allulose production where at least one step of the process involves an energetically favorable chemical reaction. Furthermore, there is a need for production process where the process steps can be conducted in one tank or bioreactor. There is also a need for a process of allulose production that can be conducted at a relatively low concentration of phosphate, where phosphate can be recycled, and/or the process does not require using adenosine triphosphate (ATP) as a source of phosphate. There is also a need for an allulose production pathway that does not require the use of the costly nicotinamide adenosine dinucleotide (NAD(H)) coenzyme in any of the reaction steps.

SUMMARY OF THE INVENTION

The inventions described herein relate to processes for preparing allulose. In various aspects, the processes involve converting fructose 6-phosphate (F6P) to allulose 6-phosphate (A6P), catalyzed by allulose 6-phosphate 3-epimerase (A6PE); and converting the A6P to allulose, catalyzed by allulose 6-phosphate phosphatase (A6PP). The inventions also relate to allulose prepared by any of the processes described herein.

In some aspects of the invention, a process for preparing allulose also involves the step of converting glucose 6-phosphate (G6P) to the F6P, where the step is catalyzed by phosphoglucoisomerase (PGI). In other aspects, a process for allulose synthesis also includes the step of converting glucose 1-phosphate (G1P) to the G6P, and this conversion step is catalyzed by phosphoglucomutase (PGM).

In various aspects, a process for preparing allulose can involve converting a saccharide to the G1P, catalyzed by at least one enzyme; converting G1P to G6P, catalyzed by phosphoglucomutase (PGM); converting G6P to F6P, catalyzed by phosphoglucoisomerase (PGI); converting F6P to allulose 6-phosphate (A6P), catalyzed by A6PE; and converting the A6P produced to allulose, catalyzed by A6PP.

The saccharides used in any of the processes can be selected from the group consisting of a starch or its derivative, cellulose or its derivative, and sucrose. The starch or its derivative can be amylose, amylopectin, soluble starch, amylodextrin, maltodextrin, maltose, or glucose. In some aspects of the invention, a process for preparing allulose involves converting starch to a starch derivative by enzymatic hydrolysis or by acid hydrolysis of starch. In other aspects, a starch derivative can be prepared by enzymatic hydrolysis of starch catalyzed by isoamylase, pullulanase, alpha-amylase, or a combination of two or more of these enzymes. A process for preparing allulose, in certain aspects, can also involve adding 4-glucan transferase (4GT).

In various aspects, a process for preparing allulose can involve converting fructose to the F6P, catalyzed by at least one enzyme; converting F6P to allulose 6-phosphate (A6P) catalyzed by A6PE; and converting the A6P produced to allulose, catalyzed by A6PP. In other embodiments, allulose production process involves converting sucrose to the fructose, catalyzed by at least one enzyme; converting fructose to the F6P, catalyzed by at least one enzyme; converting F6P to allulose 6-phosphate (A6P) catalyzed by A6PE; and converting the A6P produced to allulose, catalyzed by A6PP.

In other aspects of the invention, G6P to be used in a process for preparing allulose can be generated by converting glucose to the G6P, catalyzed by at least one enzyme. Glucose can in turn be produced by converting sucrose to glucose, catalyzed by at least one enzyme.

In other aspects of the invention, the steps of a process for preparing allulose are conducted ATP-free, NAD(H)-free, at a phosphate concentration from about 0 mM to about 150 mM, the phosphate is recycled, and/or at least one step of the process involves an energetically favorable chemical reaction.

BRIEF DESCRIPTION OF THE FIGURES

These drawings illustrate certain aspects of some of the embodiments of the invention, and should not be used to limit or define the invention.

DETAILED DESCRIPTION OF THE INVENTION

The invention provides enzymatic pathways, or processes, for synthesizing allulose with a high product yield, while greatly decreasing the product separation costs and allulose production costs.

Figure 1:
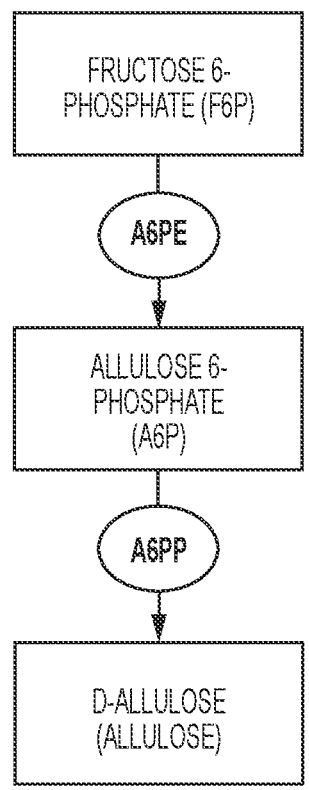
FIG. 1 is a schematic diagram illustrating an enzymatic pathway converting fructose 6-phosphate to allulose 6-phosphate and then to allulose.

The invention relates to a process for preparing allulose where the process involves converting fructose 6-phosphate (F6P) to allulose 6-phosphate (A6P) catalyzed by an epimerase and converting the A6P produced to allulose catalyzed by a phosphatase (e.g., allulose 6-phosphate phosphatase, A6PP). This process is generally shown in FIG. 1. In certain embodiments, the epimerase that catalyzes the conversion of F6P to A6P is allulose 6-phosphate 3-epimerase (A6PE).

Epimerases that convert F6P to A6P may be used in a process of the invention. Epimerases are also capable of converting A6P to F6P. In some aspects of the invention, epimerases suitable for use in the processes to convert F6P to A6P comprise an amino acid sequence that has a degree of identity to the amino acid sequence of SEQ ID NOs.: 3 or 6, of at least 45%, more preferably at least 50%, more preferably at least 55%, more preferably at least 60%, more preferably at least 65%, more preferably at least 70%, more preferably at least 75%, more preferably at least 80%, more preferably at least 85%, even more preferably at least 90%, at least 91%, at least 92%, at least 93%, or at least 94%, most preferably at least 95%, and even most preferably at least 96, 97, 98, 99 or 100%. The suitable epimerases are encoded by a polynucleotide comprising a nucleotide sequence that has a degree of identity to the nucleotide sequence of SEQ ID NOS.: 1, 2, 4, and 5; of at least 30%, preferably at least 35%, more preferably at least 40%, more preferably at least 45%, more preferably at least 50%, more preferably at least 55%, more preferably at least 60%, more preferably at least 65%, more preferably at least 70%, more preferably at least 75%, more preferably at least 80%, more preferably at least 85%, even more preferably at least 90%, most preferably at least 95%, and even most preferably at least 96, 97, 98, 99 or 100%.

Examples of A6PEs include, but are not limited to the following proteins, identified by UNIPROT ID numbers: D9TQJ4, A0A090IXZ8, and P32719. Of these, D9TQJ4 and A0A090IXZ8 are obtained from thermophilic organisms. P32719 is obtained from a mesophilic organism. P32719 is 53% identical to A0A090IXZ8 and 55% identical to D9TQJ4, and each protein catalyzes the epimerization of F6P to A6P. Furthermore, A0A090IXZ8 is 45% identical to D9TQJ4. Conversely, other epimerase proteins identified by UNIPROT ID numbers: A0A101D823, R1AXD6, A0A150LBU8, A0A023CQG9, and H1XWY2, which have a degree of identity to D9TQJ4 of 45% or less do not catalyze the epimerization of F6P to A6P.

In some aspects of the invention, epimerases suitable for use in the processes to convert F6P to A6P utilize a divalent metal cofactor: preferably, but not limited to, cobalt. In further aspects of the invention the epimerase contains but is not limited to containing an $(\alpha/\beta)_8$-barrel domain for catalysis; additionally but not limited to containing a phosphate binding domain including a Ser at the end of the $7^{th}$ β-strand of the barrel, a Ser at the end of the $8^{th}$ β-strand of the barrel, and a Gly in the active site loop; additionally but not limited to containing a metal binding domain including a His in the $2^{nd}$ and $3^{rd}$ β-strands of the barrel; additionally but not limited to containing an Asp in the $2^{nd}$ and $7^{th}$ β-strand of the barrel to act as the acid/base catalyst for 1,1 proton transfer, and additionally but not limited to containing a His-hydrophobic residue-Asp signature in the $2^{nd}$ β-strand of the barrel where the His is utilized in metal binding and the Asp for acid/base catalysis. These features are known in the art, and are referenced in, for example, Chan et al., Structural Basis for Substrate Specificity in Phosphate Binding (beta/alpha) 8-Barrels: D-Allulose 6-Phosphate 3-Epimerase from *Escherichia coli* K-12. Biochemistry. 2008; 47 (36); 9608-9617. Preferably, an epimerase for use in the processes of the invention contains an $(\alpha/\beta)_8$-barrel domain for catalysis, a Ser at the end of the 7th β-strand of the barrel, a Ser at the end of the 8th β-strand of the barrel, a Gly in the active site loop, a His in the 2nd and 3rd β-strands of the barrel, an Asp in the 2nd and 7th β-strand of the barrel, and a His-hydrophobic residue-Asp signature in the 2nd β-strand of the barrel.

Processes of the invention use phosphatases that convert A6P to allulose (D-allulose). In some aspects of the invention, phosphatases suitable for the process to convert A6P to allulose comprise an amino acid sequence that has a degree of identity to the amino acid sequence of SEQ ID NO.: 9, of at least 45%, more preferably at least 50%, more preferably at least 55%, more preferably at least 60%, more preferably at least 65%, more preferably at least 70%, more preferably at least 75%, more preferably at least 80%, more preferably at least 85%, even more preferably at least 90%, most preferably at least 95%, at least 91%, at least 92%, at least 93%, or at least 94%, and even most preferably at least 96, 97, 98, 99 or 100%. The suitable epimerases are encoded by a polynucleotide comprising a nucleotide sequence that has a degree of identity to the nucleotide sequence of SEQ ID NOS.: 7 and 8; of at least 30%, preferably at least 35%, more preferably at least 40%, more preferably at least 45%, more preferably at least 50%, more preferably at least 55%, more preferably at least 60%, more preferably at least 65%, more preferably at least 70%, more preferably at least 75%, more preferably at least 80%, more preferably at least 85%, even more preferably at least 90%, most preferably at least 95%, and even most preferably at least 96, 97, 98, 99 or 100%.

Examples of A6PPs include, but are not limited to the following proteins, identified by UNIPROT ID numbers: A3DC21, Q5LGR4, and Q89ZR1. A3DC21 is 46% identical to Q5LGR4 and 45% identical to Q89ZR1, and each protein catalyzes the specific dephosphorylation of A6P to allulose. Conversely, other phosphatases from the haloacid dehydrogenase super family, proteins identified by UNIPROT ID numbers: H0UQ29, Q67LU4, A0A0K6IPM3, C8WSJ0, A0A151YX61, and others, which are less than 45% identical to A3DC21 do not catalyze the specific dephosphorylation of A6P to allulose.

Phosphatases to convert A6P to allulose, suitable for use in the processes of the invention are specific to allulose 6-phosphate. As used herein, specific to allulose 6-phosphate refers to having a higher specific activity on allulose 6-phosphate compared to glucose 1-phosphate, glucose 6-phosphate, or fructose 6-phosphate.

Phosphatases to convert A6P to allulose utilize a divalent metal cofactor: preferably magnesium. In further aspects of the invention the phosphatase contains but is not limited to containing a Rossmanoid fold domain for catalysis; additionally but not limited to containing a C1 capping domain for substrate specificity; additionally but not limited to containing a DxD signature in the $1^{st}$ β-strand of the Rossmanoid fold for coordinating magnesium where the second Asp is a general acid/base catalyst; additionally but not limited to containing a Thr or Ser at the end of the $2^{nd}$ β-strand of the Rossmanoid fold that helps stability of reaction intermediates; additionally but not limited to containing a Lys at the N-terminus of the a-helix C-terminal to the $3^{rd}$ β-strand of the Rossmanoid fold that helps stability of reaction intermediates; and additionally but not limited to containing a GDxxxD signature at the end of the $4^{th}$ β-strand of the Rossmanoid fold for coordinating magnesium. These features are known in the art and are referenced in, for example, Burroughs et al., Evolutionary Genomics of the HAD Superfamily: Understanding the Structural Adaptations and Catalytic Diversity in a Superfamily of Phosphoesterases and Allied Enzymes. J. Mol. Biol. 2006; 361; 1003-1034. Preferably, a phosphatase to convert A6P to allulose used in the processes of the invention contains a Rossmanoid fold domain for catalysis, a C1 capping domain, DxD signature in the 1st β-strand of the Rossmanoid fold, a Thr or Ser at the end of the 2nd β-strand of the Rossmanoid fold, a Lys at the N-terminus of the α-helix C-terminal to the 3rd β-strand of the Rossmanoid fold, and a GDxxxD signature at the end of the 4th β-strand of the Rossmanoid fold.

In some embodiments, a process for preparing allulose according to the invention also includes the step of enzymatically converting glucose 6-phosphate (G6P) to the F6P, and this step is catalyzed by phosphoglucoisomerase (PGI). In other embodiments, the process for preparing allulose additionally includes the step of converting glucose 1-phosphate (G1P) to the G6P, where the step is catalyzed by phosphoglucomutase (PGM). In yet further embodiments, allulose production process also includes the step of converting a saccharide to the G1P that is catalyzed at least one enzyme.

Figure 2:
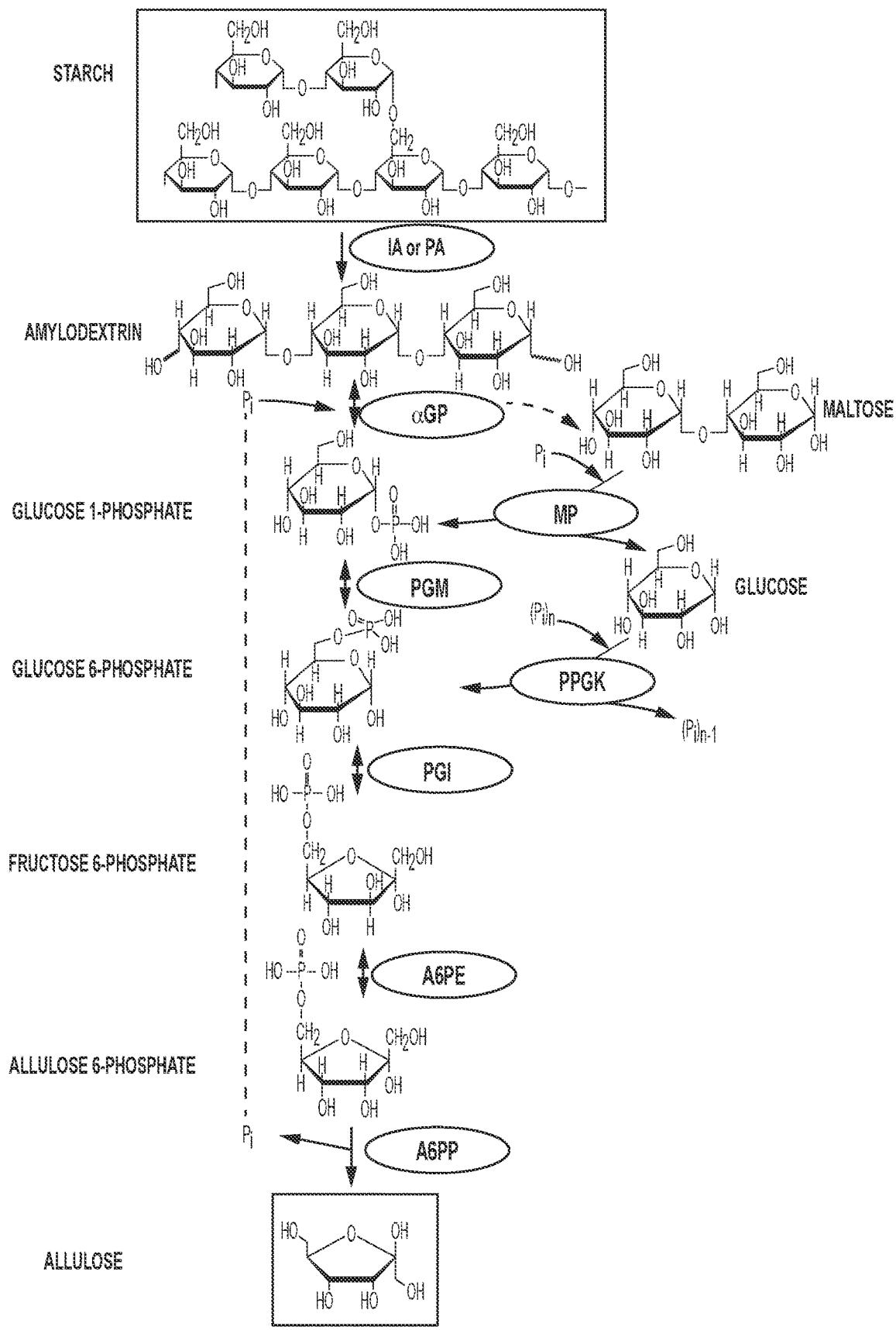
FIG. 2 is a schematic diagram illustrating an enzymatic pathway converting starch or its derived products to allulose. The following abbreviations are used: αGP, alpha-glucan phosphorylase or starch phosphorylase; PGM, phosphoglucomutase; PGI, phosphoglucoisomerase; IA, isoamylase; PA, pullulanase; MP, maltose phosphorylase; PPGK, polyphosphate glucokinase.

Therefore, a process for preparing allulose according to the invention can, for example, include the following steps: (i) converting a saccharide to glucose 1-phosphate (G1P) using one or more enzymes; (ii) converting G1P to G6P using phosphoglucomutase (PGM, EC 5.4.2.2); (iii) converting G6P to F6P using phosphoglucoisomerase (PGI, EC 5.3.1.9); (iv) converting F6P to A6P via A6PE, and (v) converting A6P to allulose via A6PP. An example of the process where the saccharide is starch is shown in FIG. 2.

Typically, the ratios of enzyme units used in the disclosed process are 1:1:1:1:1 (αGP:PGM:PGI:A6PE:A6PP). To optimize product yields, these ratios can be adjusted in any number of combinations. For example, a ratio of 3:1:1:1:1 can be used to maximize the concentration of phosphorylated intermediates, which will result in increased activity of the downstream reactions. Conversely, a ratio of 1:1:1:1:3 can be used to maintain a robust supply of phosphate for αGP, which will result in more efficient phosphorolytic cleavage of alpha-1,4-glycosidic bonds. A ratio of enzymes, for example, 3:1:1:1:3 can be used to further increase the reaction rate. Therefore, the enzyme ratios, including other optional enzymes discussed below, can be varied to increase the efficiency of allulose production. For example, a particular enzyme may be present in an amount about 2×, 3×, 4×, 5×, etc. relative to the amount of other enzymes.

One of the important advantages of the processes is that the process steps can be conducted in one bioreactor or reaction vessel. Alternatively, the steps can also be conducted in a plurality of bioreactors, or reaction vessels, that are arranged in series.

Phosphate ions produced by dephosphorylation of A6P can then be recycled in the process step of converting a saccharide to G1P, particularly when all process steps are conducted in a single bioreactor or reaction vessel. The ability to recycle phosphate in the disclosed processes allows for non-stoichiometric amounts of phosphate to be used, which keeps reaction phosphate concentrations low. This affects the overall pathway and the overall rate of the processes, but does not limit the activity of the individual enzymes and allows for overall efficiency of the allulose making processes.

For example, reaction phosphate concentrations can range from about 0 mM to about 300 mM, from about 0 mM to about 150 mM, from about 1 mM to about 50 mM, preferably from about 5 mM to about 50 mM, or more preferably from about 10 mM to about 50 mM. For instance, the reaction phosphate concentration can be about 0.1 mM, about 0.5 mM, about 1 mM, about 1.5 mM, about 2 mM, about 2.5 mM, about 5 mM, about 6 mM, about 7 mM, about 8 mM, about 9 mM, about 10 mM, about 15 mM, about 20 mM, about 25 mM, about 30 mM, about 35 mM, about 40 mM, about 45 mM, about 50 mM, or about 55 mM.

Therefore, low phosphate concertation results in decreased production costs due to low total phosphate and thus lowered cost of phosphate removal. It also prevents inhibition of the A6PP by high concentrations of free phosphate and decreases the potential for phosphate pollution.

Figure 7:
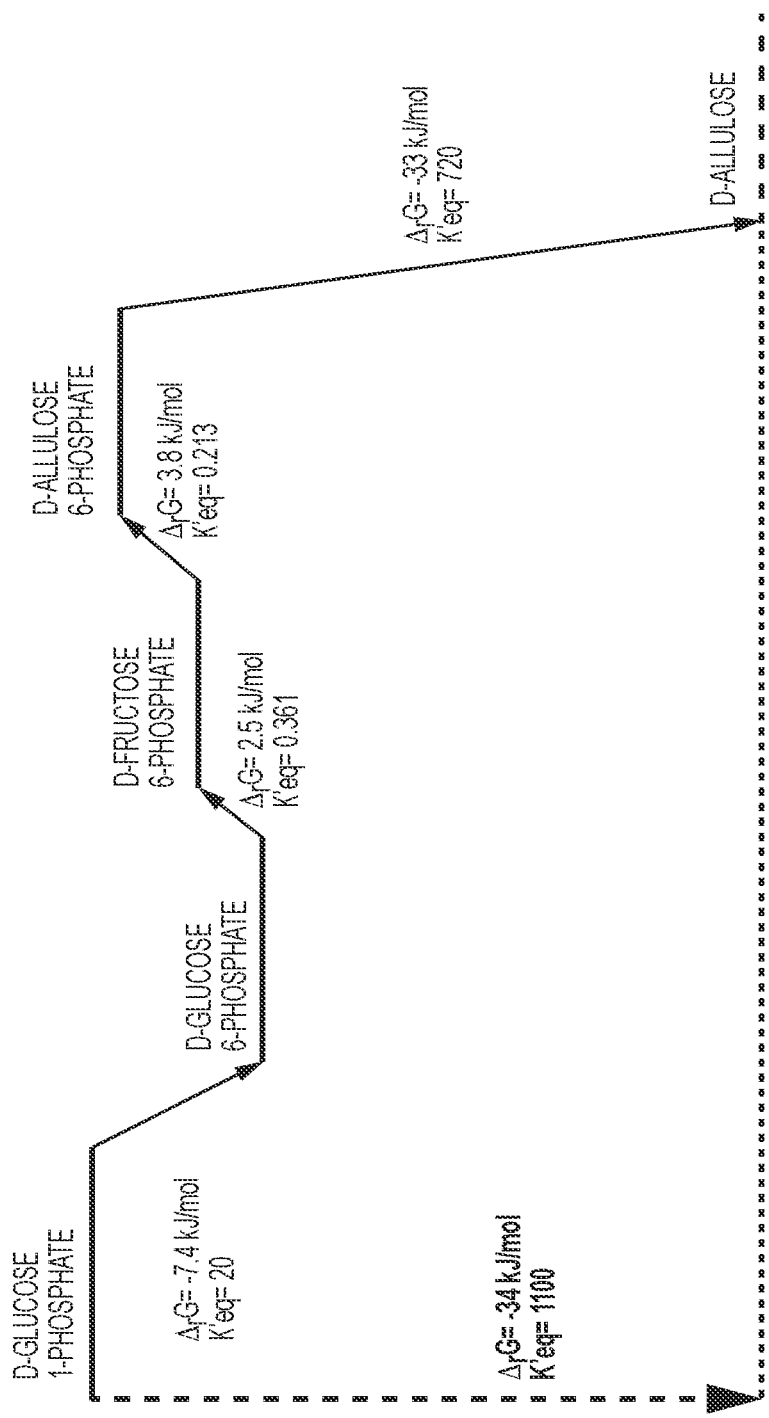
FIG. 7 shows the Reaction Gibbs Energy between intermediates based on formation Gibbs energy for the conversion of glucose 1-phosphate to allulose.

Furthermore, the processes disclosed herein can be conducted without added ATP as a source of phosphate, i.e., ATP-free. The processes can also be conducted without having to add NAD(H), i.e., NAD(H)-free. Other advantages also include the fact that at least one step of the disclosed processes for making allulose involves an energetically favorable chemical reaction (FIG. 7).

Examples of the enzymes used to convert a saccharide to G1P include alpha-glucan phosphorylase (αGP, EC 2.4.1.1 which also includes maltodextrin phosphorylase, starch phosphorylase, glycogen phosphorylase, and other α-1,4 glycosidic bond degrading phosphorylases), maltose phosphorylase (MP, EC 2.4.1.8), cellodextrin phosphorylase (CDP, EC 2.4.1.49), cellobiose phosphorylase (CBP, EC 2.4.1.20), cellulose phosphorylase, sucrose phosphorylase (SP, EC 2.4.1.7), and a combination thereof. The choice of the enzyme or enzyme combination depends on the saccharide used in the process.

The saccharides used for generating G1P can be polysaccharides, oligosaccharides, and/or disaccharides. For example, the saccharide can be starch, one or more derivatives of starch, cellulose, one or more derivatives of cellulose, sucrose, one or more derivatives of sucrose, or a combination thereof.

Starch is the most widely used energy storage compound in nature and is mostly stored in plant seeds. Natural starch contains linear amylose and branched amylopectin. Examples of starch derivatives include amylose, amylopectin, soluble starch, amylodextrin, maltodextrin, maltose, fructose, and glucose. Examples of cellulose derivatives include pretreated biomass, regenerated amorphous cellulose, cellodextrin, cellobiose, fructose, and glucose. Sucrose derivatives include fructose and glucose.

The derivatives of starch can be prepared by enzymatic hydrolysis of starch or by acid hydrolysis of starch. Specifically, the enzymatic hydrolysis of starch can be catalyzed or enhanced by isoamylase (IA, EC. 3.2.1.68), which hydrolyzes α-1,6-glucosidic bonds; pullulanase (PA, EC. 3.2.1.41), which hydrolyzes α-1,6-glucosidic bonds; 4-α-glucanotransferase (4GT, EC. 2.4.1.25), which catalyzes the transglycosylation of short maltooligosaccharides, yielding longer maltooligosaccharides; or alpha-amylase (EC 3.2.1.1), which cleaves α-1,4-glucosidic bonds.

Furthermore, derivatives of cellulose can be prepared by enzymatic hydrolysis of cellulose catalyzed by cellulase mixtures, by acids, or by pretreatment of biomass.

In certain embodiments, the enzymes used to convert a saccharide to G1P contain αGP. In this step, when the saccharides include starch, the G1P is generated from starch by αGP; when the saccharides contain soluble starch, amylodextrin, or maltodextrin, the G1P is produced from soluble starch, amylodextrin, or maltodextrin by αGP.

When the saccharides include maltose and the enzymes contain maltose phosphorylase, the G1P is generated from maltose by maltose phosphorylase. If the saccharides include sucrose, and enzymes contain sucrose phosphorylase, the G1P is generated from sucrose by sucrose phosphorylase.

In yet another embodiment, when the saccharides include cellobiose, and the enzymes contain cellobiose phosphorylase, the G1P is generated from cellobiose by cellobiose phosphorylase.

In an additional embodiment, when the saccharides contain cellodextrins and the enzymes include cellodextrin phosphorylase, the G1P is generated from cellodextrins by cellodextrin phosphorylase.

In an alternative embodiment of converting a saccharide to G1P, when the saccharides include cellulose, and enzymes contain cellulose phosphorylase, the G1P is generated from cellulose by cellulose phosphorylase.

Figure 4:
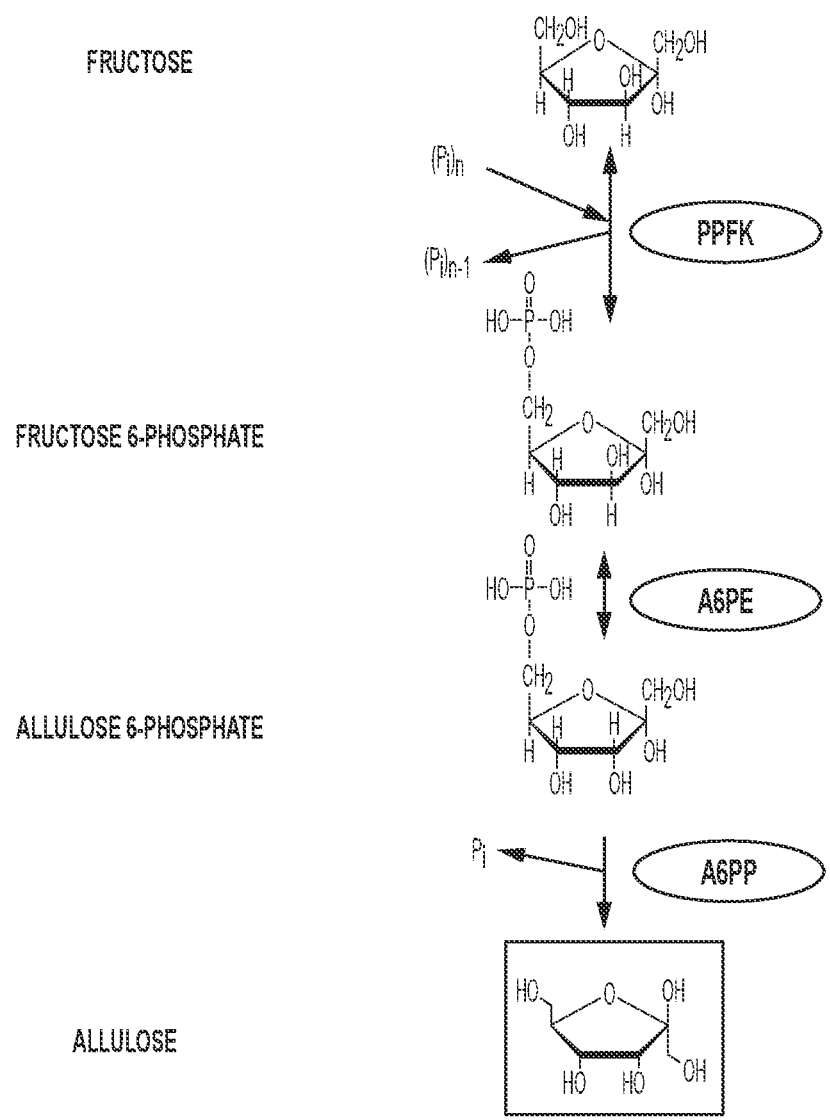
FIG. 4 is a schematic diagram illustrating an enzymatic pathway converting fructose to allulose. PPFK, polyphosphate fructokinase.

According to the invention, allulose can also be produced from fructose. An example of the process is shown in FIG. 4. For example, the process involves generating F6P from fructose and polyphosphate catalyzed by polyphosphate fructokinase (PPFK); converting F6P to A6P catalyzed by A6PE; and converting A6P to allulose catalyzed by A6PP. The fructose can be produced, for example, by an enzymatic conversion of sucrose.

Figure 6:
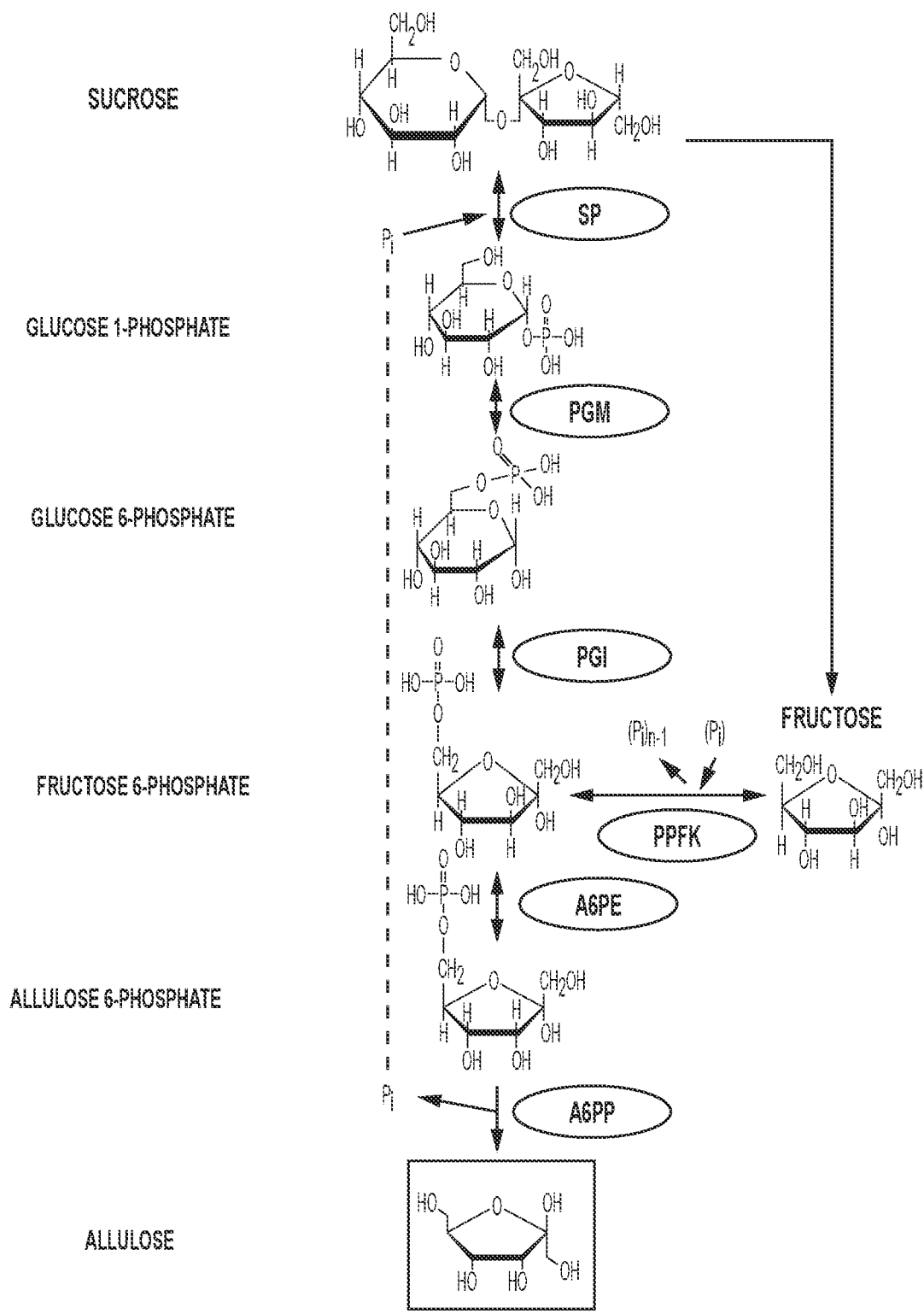
FIG. 6 shows an enzymatic pathway converting sucrose or its derived products to allulose. SP, sucrose phosphorylase; PPFK, polyphosphate fructokinase; PGM, phosphoglucomutase; PGI, phosphoglucoisomerase.

In other embodiments, allulose can be produced from sucrose. An example of such process is shown in FIG. 6. The process provides an in vitro synthetic pathway that includes the following enzymatic steps: generating G1P from sucrose and free phosphate catalyzed by sucrose phosphorylase (SP); converting G1P to G6P catalyzed by PGM; converting G6P to F6P catalyzed by PGI; converting F6P to A6P catalyzed by A6PE; and converting A6P to allulose catalyzed by A6PP.

The phosphate ions generated when A6P is converted to allulose can then be recycled in the step of converting sucrose to G1P. Additionally, as shown in FIG. 6, PPFK and polyphosphate can be used to increase allulose yields by producing F6P from fructose generated by the phosphorolytic cleavage of sucrose by SP.

In some embodiments, a process for preparing allulose includes the following steps: generating glucose from polysaccharides and oligosaccharides by enzymatic hydrolysis or acid hydrolysis, converting glucose to G6P catalyzed by at least one enzyme, generating fructose from polysaccharides and oligosaccharides by enzymatic hydrolysis or acid hydrolysis, and converting fructose to G6P catalyzed by at least one enzyme. Examples of the polysaccharides and oligosaccharides are enumerated above.

In other embodiments, G6P is produced from glucose and sodium polyphosphate by polyphosphate glucokinase.

The present disclosure provides processes for converting saccharides, such as polysaccharides and oligosaccharides in starch, cellulose, sucrose and their derived products, to allulose. In certain embodiments, artificial (non-natural) ATP-free enzymatic pathways are provided to convert starch, cellulose, sucrose, and their derived products to allulose using cell-free enzyme cocktails.

As shown above, several enzymes can be used to hydrolyze starch to increase the G1P yield. Such enzymes include isoamylase, pullulanase, and alpha-amylase. Corn starch contains many branches that impede αGP action. Isoamylase can be used to de-branch starch, yielding linear amylodextrin. Isoamylase-pretreated starch can result in a higher F6P concentration in the final product. Isoamylase and pullulanase cleave alpha-1,6-glycosidic bonds, which allows for more complete degradation of starch by alpha-glucan phosphorylase. Alpha-amylase cleaves alpha-1,4-glycosidic bonds, therefore alpha-amylase is used to degrade starch into fragments for quicker conversion to allulose.

As shown in FIG. 2, maltose phosphorylase (MP) can be used to increase allulose yields by phosphorolytically cleaving the degradation product maltose into G1P and glucose. Alternatively, 4-glucan transferase (4GT) can be used to increase allulose yields by recycling the degradation products glucose, maltose, and maltotriose into longer maltooligosaccharides; which can be phosphorolytically cleaved by αGP to yield G1P.

Additionally, cellulose is the most abundant bio resource and is the primary component of plant cell walls. Non-food lignocellulosic biomass contains cellulose, hemicellulose, and lignin as well as other minor components. Pure cellulose, including Avicel (microcrystalline cellulose), regenerated amorphous cellulose, bacterial cellulose, filter paper, and so on, can be prepared via a series of treatments. The partially hydrolyzed cellulosic substrates include water-insoluble cellodextrins whose degree of polymerization is more than 7, water-soluble cellodextrins with degree of polymerization of 3-6, cellobiose, glucose, and fructose.

In certain embodiments, cellulose and its derived products can be converted to allulose through a series of steps. An example of such process is a shown in FIG. 3. The process provides an in vitro synthetic pathway that involves the following steps: generating G1P from cellodextrin and cellobiose and free phosphate catalyzed by cellodextrin phosphorylase (CDP) and cellobiose phosphorylase (CBP), respectively; converting G1P to G6P catalyzed by PGM; converting G6P to F6P catalyzed by PGI; converting F6P to A6P catalyzed by A6PE; and converting A6P to allulose catalyzed by A6PP. In this process, the phosphate ions can be recycled by the step of converting cellodextrin and cellobiose to G1P.

Several enzymes may be used to hydrolyze solid cellulose to water-soluble cellodextrins and cellobiose. Such enzymes include endoglucanase and cellobiohydrolase, but not including beta-glucosidase (cellobiase).

Prior to cellulose hydrolysis and G1P generation, cellulose and biomass can be pretreated to increase their reactivity and decrease the degree of polymerization of cellulose chains. Cellulose and biomass pretreatment methods include dilute acid pretreatment, cellulose solvent-based lignocellulose fractionation, ammonia fiber expansion, ammonia aqueous soaking, ionic liquid treatment, and partially hydrolyzed by using concentrated acids, including hydrochloric acid, sulfuric acid, phosphoric acid and their combinations.

Figure 3:
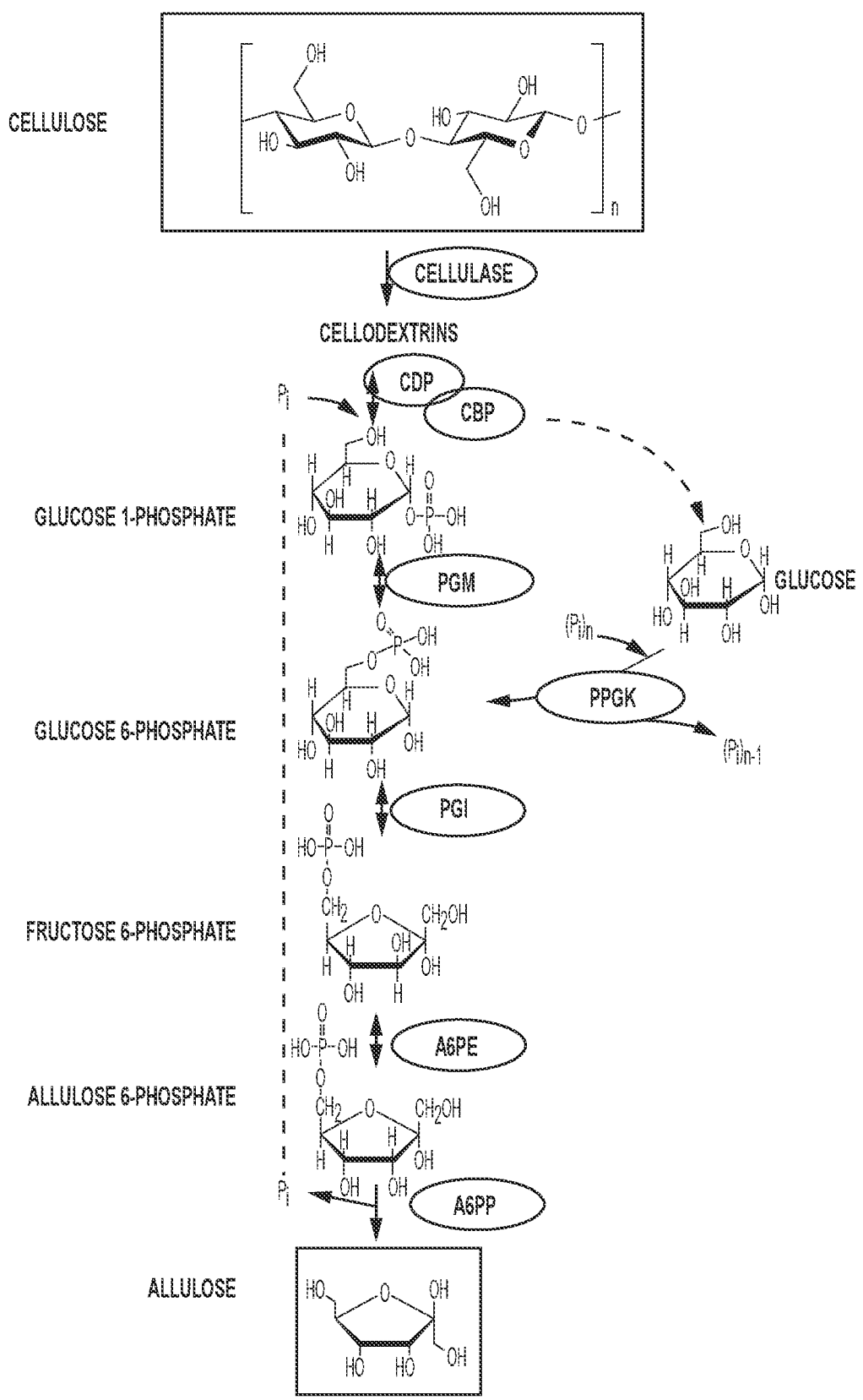
FIG. 3 shows an enzymatic pathway converting cellulose or its derived products to allulose. CDP, cellodextrin phosphorylase; CBP, cellobiose phosphorylase; PPGK, polyphosphate glucokinase☐; PGM, phosphoglucomutase; PGI, phosphoglucoisomerase.

In some embodiments, polyphosphate and polyphosphate glucokinase (PPGK) can be added to the process, thus increasing yields of allulose by phosphorylating the degradation product glucose to G6P, as shown in FIG. 3.

Figure 5:
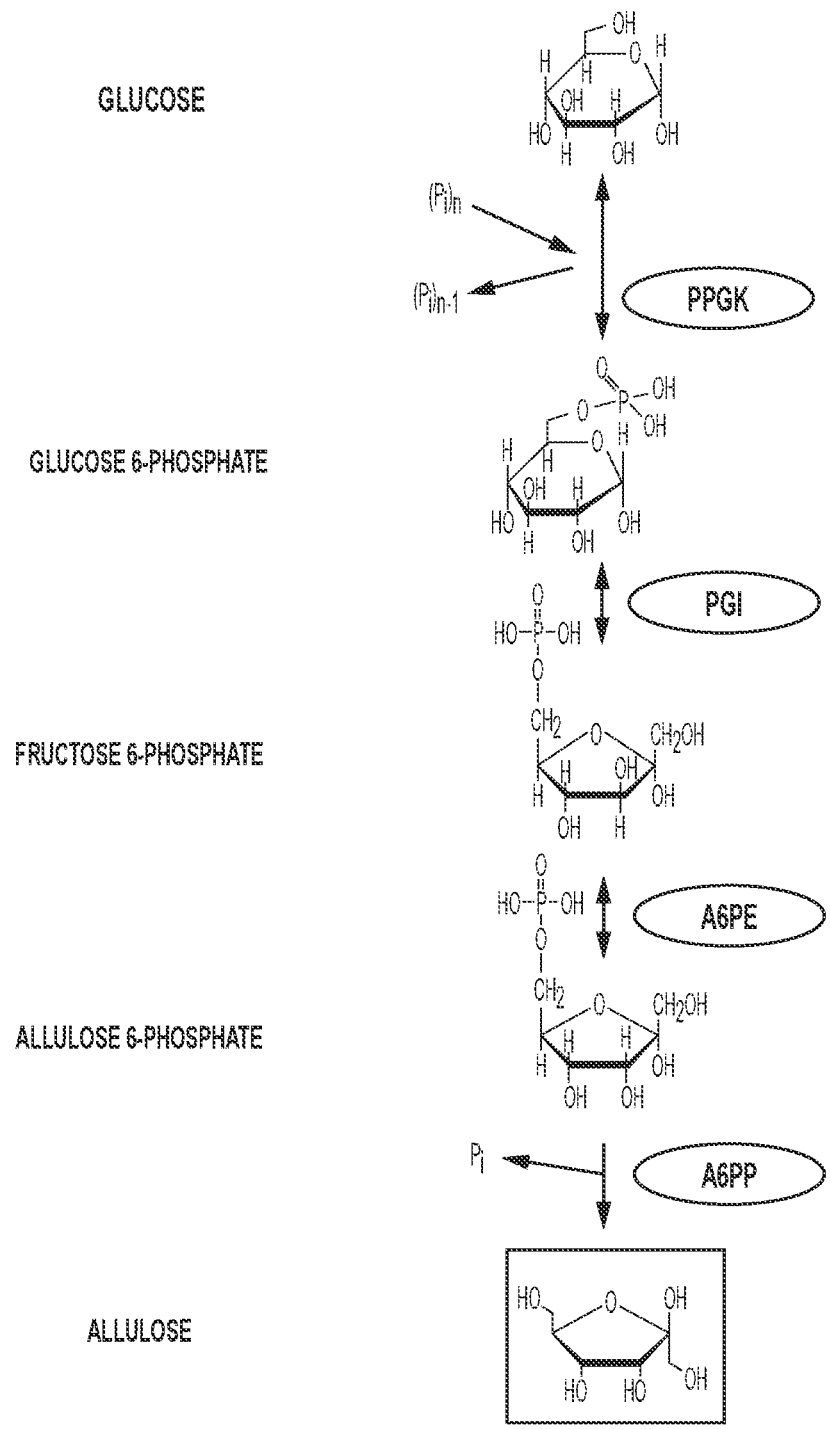
FIG. 5 is a schematic diagram illustrating an enzymatic pathway converting glucose to allulose. PPGK, polyphosphate glucokinase; PGI, phosphoglucoisomerase.

In other embodiments, allulose can be generated from glucose. An example of such process is shown in FIG. 5. The process involves the steps of generating G6P from glucose and polyphosphate catalyzed by polyphosphate glucokinase (PPGK); converting G6P to F6P catalyzed by PGI; converting F6P to A6P catalyzed by an enzyme; and converting A6P to allulose catalyzed by A6PP.

Any suitable biological buffer known in the art can be used in a process of the invention, such as HEPES, PBS, BIS-TRIS, MOPS, DIPSO, Trizma, etc. The reaction buffer for all embodiments can have a pH ranging from 5.0-8.0. More preferably, the reaction buffer pH can range from about 6.0 to about 7.3. For example, the reaction buffer pH can be 6.0, 6.2, 6.4, 6.6, 6.8, 7.0, 7.2, or 7.3.

The reaction buffer can also contain key metal cations. Examples of the metal ions include $Mg^{2+}$, $Co^{2+}$, and $Zn^{2+}$.

The reaction temperature at which the process steps are conducted can range from 37-85° C. More preferably, the steps can be conducted at a temperature ranging from about 40° C. to about 70° C. The temperature can be, for example, about 40° C., about 45° C., about 50° C., about 55° C., or about 60° C. Preferably, the reaction temperature is about 50° C.

The reaction time of the disclosed processes can be adjusted as necessary, and can range from about 8 hours to about 48 hours. For example, the reaction time can be about 16 hours, about 18 hours, about 20 hours, about 22 hours, about 24 hours, about 26 hours, about 28 hours, about 30 hours, about 32 hours, about 34 hours, about 36 hours, about 38 hours, about 40 hours, about 42 hours, about 44 hours, about 46 hours, or about 48 hours. More preferably, the reaction time is about 24 hours.

The processes according to the invention can achieve high yields due to the very favorable equilibrium constant for the overall reaction. Theoretically, up to 99% yields can be achieved if the starting material is completely converted to an intermediate.

Processes of the invention use low-cost starting materials and reduce production costs by decreasing costs associated with the feedstock and product separation. Starch, cellulose, sucrose and some of their derivatives are less expensive feedstocks than, for example, fructose. When allulose is produced from fructose, yields are lower than in the present invention, and allulose must be separated from fructose via chromatography, which leads to higher production costs.

Also, the step of converting A6P to allulose according to the invention is an irreversible phosphatase reaction, regardless of the feedstock. Therefore, allulose is produced with a very high yield while effectively minimizing the subsequent product separation costs.

In contrast to cell-based manufacturing methods, the invention involves a cell-free preparation of allulose, has relatively high reaction rates due to the elimination of the cell membrane, which often slows down the transport of substrate/product into and out of the cell. It also has a final product free of nutrient-rich fermentation media/cellular metabolites.

EXAMPLES

Materials and Methods
Chemicals

All chemicals, including corn starch, soluble starch, maltodextrins, maltose, glucose, filter paper were reagent grade or higher and purchased from Sigma-Aldrich (St. Louis, Mo., USA) or Fisher Scientific (Pittsburgh, Pa., USA), unless otherwise noted. Restriction enzymes, T4 ligase, and Phusion DNA polymerase were purchased from New England Biolabs (Ipswich, Mass., USA). Oligonucleotides were synthesized either by Integrated DNA Technologies (Coralville, Iowa, USA) or Eurofins MWG Operon (Huntsville, Ala., USA). The nucleotide sequence, SEQ ID NO 1, encodes for Thermophilic A6PE from *Thermoanaerobacterium thermosaccharolyticum* (UNIPROT ID D9TQJ4). SEQ ID NO 2 is a codon optimized version of that nucleotide sequence. SEQ ID NO 3 is the amino acid sequence for the enzyme. The nucleotide sequence SEQ ID NO 4 encodes for Thermophilic A6PE from *Bacillus thermoamylovorans* (UNIPROT ID A0A090IXZ8). SEQ ID NO 5 is a codon optimized version of that nucleotide sequence. SEQ ID NO 6 is the amino acid sequence for the enzyme. The nucleotide sequence SEQ ID NO 7 encodes for Thermophilic A6PP from *Clostridium thermocellum* (UNIPROT ID A3DC21). SEQ ID NO 8 is a codon optimized version of the nucleotide sequence. SEQ ID NO 9 is the amino acid sequence corresponding to the enzyme. Regenerated amorphous cellulose used in enzyme purification was prepared from Avicel PH105 (FMC BioPolymer, Philadelphia, Pa., USA) through its dissolution and regeneration, as described in: Ye et al., *Fusion of a family 9 cellulose-binding module improves catalytic potential of Clostridium thermocellum cellodextrin phosphorylase on insoluble cellulose.* Appl. Microbiol. Biotechnol. 2011; 92:551-560. *Escherichia coli* Sig10 (Sigma-Aldrich, St. Louis, Mo., USA) was used as a host cell for DNA manipulation and *E. coli* BL21 (DE3) (Sigma-Aldrich, St. Louis, Mo., USA) was used as a host cell for recombinant protein expression. ZYM-5052 media including either 100 mg $L^{-1}$ ampicillin or 50 mg $L^{-1}$ kanamycin was used for *E. coli* cell growth and recombinant protein expression. Cellulase from *Trichoderma reesei* (Catalog number: C2730) and pullulanase (Catalog number: P1067) were purchased from Sigma-Aldrich (St. Louis, Mo., USA) and produced by Novozymes (Franklinton, N.C., USA). Maltose phosphorylase (Catalog number: M8284) was purchased from Sigma-Aldrich.

Production and Purification of Recombinant Enzymes

The *E. coli* BL21 (DE3) strain harboring a protein expression plasmid was incubated in a 1-L Erlenmeyer flask with 100 mL of ZYM-5052 media containing either 100 mg $L^{-1}$ ampicillin or 50 mg $L^{-1}$ kanamycin. Cells were grown at 30°

C. with rotary shaking at 220 rpm for 16-24 hours. The cells were harvested by centrifugation at 12° C. and washed once with either 20 mM HEPES (pH 7.5) containing 50 mM NaCl and 5 mM $MgCl_2$ (heat precipitation and cellulose-binding module) or 20 mM HEPES (pH 7.5) containing 300 mM NaCl and 5 mM imidazole (Ni purification). The cell pellets were re-suspended in the same buffer and lysed by ultra-sonication (Fisher Scientific Sonic Dismembrator Model 500; 5 s pulse on and 10 s off, total 21 min at 50% amplitude). After centrifugation, the target proteins in the supernatants were purified.

Three approaches were used to purify the various recombinant proteins. His-tagged proteins were purified by the Profinity IMAC Ni-Charged Resin (Bio-Rad, Hercules, Calif., USA). Fusion proteins containing a cellulose-binding module (CBM) and self-cleavage intein were purified through high-affinity adsorption on a large surface-area regenerated amorphous cellulose. Heat precipitation at 70-95° C. for 5-30 min was used to purify hyperthermostable enzymes. The purity of the recombinant proteins was examined by sodium dodecyl sulfate polyacrylamide gel electrophoresis (SDS-PAGE). A6PE was purified with 80 µM $CoCl_2$ present in growth media, elution buffers, dialysis buffer, and protein storage buffer.

Enzymes Used and Their Activity Assays

Alpha-glucan phosphorylase (αGP) from *Thermotoga maritima* (UNIPROT ID G4FEH8) was used. Activity was assayed in 50 mM sodium phosphate buffer (pH 7.2) containing 1 mM $MgCl_2$, 5 mM DTT, and 30 mM maltodextrin at 50° C. The reaction was stopped via filtration of enzyme with a Vivaspin 2 concentrator (10,000 MWCO) (Vivaproducts, Inc., Littleton, Mass., USA). Glucose 1-phosphate (G1P) was measured using a glucose hexokinase/G6PDH assay kit (Sigma Aldrich, Catalog No. GAHK20-1KT) supplemented with 25 U/mL phosphoglucomutase. A unit (U) is described as µmol/min.

Phosphoglucomutase (PGM) from *Thermococcus kodakaraensis* (UNIPROT ID Q68BJ6) was used. Activity was measured in 50 mM HEPES buffer (pH 7.2) containing 5 mM $MgCl_2$ and 5 mM G1P at 50° C. The reaction was stopped via filtration of enzyme with a Vivaspin 2 concentrator (10,000 MWCO). The product glucose 6-phosphate (G6P) was determined using a hexokinase/G6PDH assay kit (Sigma Aldrich, Catalog No. GAHK20-1KT).

Two different sources of phosphoglucoisomerase (PGI) were used from *Clostridium thermocellum* (UNIPROT ID A3DBX9) and *Thermus thermophilus* (UNIPROT ID Q5SLL6). Activity was measured in 50 mM HEPES buffer (pH 7.2) containing 5 mM $MgCl_2$ and 10 mM G6P at 50° C. The reaction was stopped via filtration of enzyme with a Vivaspin 2 concentrator (10,000 MWCO). The product, fructose 6-phosphate (F6P), was determined using a fructose 6-phosphate kinase (F6PK)/pyruvate dehydrogenase (PK)/lactate dehydrogenase (LD) coupled enzyme assay where a decrease in absorbance at 340 nm indicates production of F6P. This 200 µL reaction contained 50 mM HEPES (pH 7.2), 5 mM $MgCl_2$, 10 mM G6P, 1.5 mM ATP, 1.5 mM phosphoenol pyruvate, 200 µM NADH, 0.1 U PGI, 5 U PK, and 5 U LD.

Allulose 6-phosphate 3-epimerase (A6PE) from *Thermoanaerobacterium thermosaccharolyticum* (UNIPROT ID D9TQJ4), SEQ ID NO 3, was used. Activity was measured in 50 mM HEPES buffer (pH 7.2) containing 5 mM $MgCl_2$, 80 µM $CoCl_2$, 1 U/mL A6PP, and 10 mM F6P at 50° C. The reaction was stopped via filtration of enzyme with a Vivaspin 2 concentrator (10,000 MWCO). The product, allulose 6-phosphate (A6P), was determined using allulose 6-phosphate phosphatase and detecting free phosphate release. To detect free phosphate release, 500 µL of a solution containing 0.1 M zinc acetate and 2 mM ammonium molybdate (pH 5) was added to 50 µL of reaction. This was mixed and followed by 125 µL of 5% ascorbic acid (pH 5). This solution was mixed then incubated at 30° C. for 20 min. The absorbance at 850 nm was read to determine free phosphate release.

Allulose 6-phosphate phosphatase (A6PP) from *Clostridium thermocellum* (UNIPROT ID A3DC21), SEQ ID NO 9, was used. Activity was measured in 50 mM HEPES buffer (pH 7.2) containing 5 mM $MgCl_2$, 80 µM $CoCl_2$, 1 U/mL A6PE, and 10 mM F6P at 50° C. The reaction was stopped via filtration of enzyme with a Vivaspin 2 concentrator (10,000 MWCO). The product, allulose, was determined through detecting free phosphate release as described for A6PE.

The recombinant cellodextrin phosphorylase and cellobiose phosphorylase from *C. thermocellum* are described in Ye et al. Spontaneous high-yield production of hydrogen from cellulosic materials and water catalyzed by enzyme cocktails. ChemSusChem 2009; 2:149-152. Their activities were assayed as described.

The recombinant polyphosphate glucokinase from *Thermobifida fusca* YX is described in Liao et al., One-step purification and immobilization of thermophilic polyphosphate glucokinase from *Thermobifida fusca* YX: glucose-6-phosphate generation without ATP. Appl. Microbiol. Biotechnol. 2012; 93:1109-1117. Its activities were assayed as described.

The recombinant isoamylase from *Sulfolobus tokodaii* is described in Cheng et al., Doubling power output of starch biobattery treated by the most thermostable isoamylase from an archaeon *Sulfolobus tokodaii*. Scientific Reports 2015; 5:13184. Its activities were assayed as described.

The recombinant 4-alpha-glucanoltransferase from *Thermococcus litoralis* is described in Jeon et al. 4-α-Glucanotransferase from the Hyperthermophilic Archaeon *Thermococcus litoralis*. Eur. J. Biochem. 1997; 248:171-178. Its activity was measured as described.

Sucrose phosphorylase from *Caldithrix abyssi* (UNIPROT H1XT50) was used. Its activity was measured in 50 mM HEPES buffer (pH 7.5) containing 10 mM sucrose and 12 mM organic phosphate. Glucose 1-phosphate (G1P) was measured using a glucose hexokinase/G6PDH assay kit supplemented with 25 U/mL phosphoglucomutase as with alpha-glucan phosphorylase.

Enzyme units used in each Example below can be increased or decreased to adjust the reaction time as desired. For example, if one wanted to perform Example 9 in 8 h instead of 24 h, the units of the enzymes would be increased about 3-fold. Conversely, if one wanted perform example 9 in 48 h instead of 24 h the enzyme units could be decreased about 2-fold. These examples illustrate how the amount of enzyme units can be used to increase or decrease reaction time while maintaining constant productivity.

Example 1

To validate the technical feasibility of the enzymatic biosynthesis of fructose 6-phosphate from starch, three enzymes were recombinantly expressed: alpha-glucan phosphorylase from *T. maritima* (UNIPROT ID G4FEH8), phosphoglucomutase from *Thermococcus kodakaraensis* (UNIPROT ID Q68BJ6), and phosphoglucoisomerase from *Clostridium thermocellum* (UNIPROT ID A3DBX9). The recombinant proteins were over-expressed in *E. coli* BL21 (DE3) and purified as described above.

A 0.20 mL reaction mixture containing 10 g/L soluble starch, 50 mM phosphate buffered saline pH 7.2, 5 mM $MgCl_2$, 0.5 mM $ZnCl_2$, 0.01 U of αGP, 0.01 U PGM, and 0.01 U PGI was incubated at 50° C. for 24 hours. The reaction was stopped via filtration of enzyme with a Vivaspin 2 concentrator (10,000 MWCO). The product, fructose 6-phosphate (F6P), was determined using a fructose 6-phosphate kinase (F6PK)/pyruvate dehydrogenase (PK)/lactate dehydrogenase (LD) coupled enzyme assay where a decrease in absorbance at 340 nm indicates production of F6P as described above. The final concentration of F6P after 24 hours was 3.6 g/L.

Example 2

Same tests as in Example 1 (other than reaction temperatures) were carried out from 40 to 80° C. It was found that 10 g/L soluble starch produced 0.9 g/L F6P at 40° C. and 3.6 g/L F6P at 80° C. after 40 hour reactions. These results suggest that increasing reaction temperature for this set of enzymes increased F6P yields, but too high temperature may impair some enzyme activity.

Example 3

It was found that, at 80° C., an enzyme unit ratio of αGP: PGM: PGI of approximately 1:1:1 resulted in fast F6P generation. It was noted that the enzyme ratio did not influence final F6P concentration greatly if the reaction time was long enough. However, the enzyme ratio affects reaction rates and the total cost of enzymes used in the system.

Example 4

A 0.20 mL reaction mixture containing 10 g/L maltodextrin, 50 mM phosphate buffered saline pH 7.2, 5 mM $MgCl_2$, 0.5 mM $ZnCl_2$, 0.01 U of αGP, 0.01 U PGM, and 0.01 U PGI was incubated at 50° C. for 24 hours. The reaction was stopped via filtration of enzyme with a Vivaspin 2 concentrator (10,000 MWCO). The product, fructose 6-phosphate (F6P), was determined using a fructose 6-phosphate kinase (F6PK)/pyruvate dehydrogenase (PK)/lactate dehydrogenase (LD) coupled enzyme assay where a decrease in absorbance at 340 nm indicates production of F6P as described above. The final concentration of F6P after 24 hours was 3.6 g/L.

Example 5

To test for F6P production from Avicel, Sigma cellulase was used to hydrolyze cellulose at 50° C. To remove beta-glucosidase from commercial cellulase, 10 filter paper units/mL of cellulase was mixed to 10 g/L Avicel at an ice-water bath for 10 min. After centrifugation at 4° C., the supernatant containing beta-glucosidase was decanted. Avicel that was bound with cellulase containing endoglucanase and cellobiohydrolase was resuspended in a citrate buffer (pH 4.8) for hydrolysis at 50° C. for three days. The cellulose hydrolysate was mixed with 5 U/mL cellodextrin phosphorylase, 5 U/L cellobiose phosphorylase, 5 U/mL of αGP, 5 U/mL PGM, and 5 U/mL PGI in a 100 mM HEPES buffer (pH 7.2) containing 10 mM phosphate, 5 mM $MgCl_2$ and 0.5 mM $ZnCl_2$. The reaction was conducted at 60° C. for 72 hours and high concentrations of F6P were found (small amounts of glucose and no cellobiose). F6P was detected using the coupled enzyme assay described above. Glucose was detected using a hexokinase/G6PDH assay kit as described above.

Example 6

To increase F6P yields from Avicel, Avicel was pretreated with concentrated phosphoric acid to produce amorphous cellulose (RAC), as described in Zhang et al. *A transition from cellulose swelling to cellulose dissolution by o-phosphoric acid: evidence from enzymatic hydrolysis and supramolecular structure.* Biomacromolecules 2006; 7:644-648. To remove beta-glucosidase from commercial cellulase, 10 filter paper units/mL of cellulase was mixed with 10 g/L RAC in an ice-water bath for 5 min. After centrifugation at 4° C., the supernatant containing beta-glucosidase was decanted. The RAC that was bound with cellulase containing endoglucanase and cellobiohydrolase was resuspended in a citrate buffer (pH 4.8) for hydrolysis at 50° C. for 12 hours. The RAC hydrolysate was mixed with 5 U/mL cellodextrin phosphorylase, 5 U/L cellobiose phosphorylase, 5 U/mL of αGP, 5 U/mL PGM, and 5 U/mL PGI in a 100 mM HEPES buffer (pH 7.2) containing 10 mM phosphate, 5 mM $MgCl_2$ and 0.5 mM $ZnCl_2$. The reaction was conducted at 60° C. for 72 hours. High concentrations of F6P and glucose were recovered because no enzymes were added to convert glucose to F6P. F6P was detected using the coupled enzyme assay described above. Glucose was detected using a hexokinase/G6PDH assay kit as described above.

Example 7

To further increase F6P yields from RAC, polyphosphate glucokinase and polyphosphate were added. To remove beta-glucosidase from commercial cellulase, 10 filter paper units/mL of cellulase was mixed with 10 g/L RAC in an ice-water bath for 5 min. After centrifugation at 4° C., the supernatant containing beta-glucosidase was decanted. The RAC that was bound with cellulase containing endoglucanase and cellobiohydrolase was re-suspended in a citrate buffer (pH 4.8) for hydrolysis at 50° C. was incubated in a citrate buffer (pH 4.8) for hydrolysis at 50° C. for 12 hours. The RAC hydrolysate was mixed with 5 U/mL polyphosphate glucokinase, 5 U/mL cellodextrin phosphorylase, 5 U/mL cellobiose phosphorylase, 5 U/mL of αGP, 5 U/mL PGM, and 5 U/mL PGI in a 100 mM HEPES buffer (pH 7.2) containing 50 mM polyphosphate, 10 mM phosphate, 5 mM $MgCl_2$ and 0.5 mM $ZnCl_2$. The reaction was conducted at 50° C. for 72 hours. F6P was found in high concentrations with only small amounts of glucose now present. F6P was detected using the coupled enzyme assay described above. Glucose was detected using a hexokinase/G6PDH assay kit as described above.

Example 8

To validate allulose production from F6P, 2 g/L F6P was mixed with 1 U/ml A6PE and 1 U/ml A6PP in 50 mM HEPES buffer (pH 7.2) containing 5 mM $MgCl_2$ and 80 μM $CoCl_2$. The reaction was incubated for 6 hours at 50° C. 99% conversion of F6P to allulose was seen via HPLC (Agilent 1100 series) using an Agilent Hi-Plex H-column and refractive index detector. The sample was run in 5 mM $H_2SO_4$ at 0.6 mL/min.

Example 9

To validate production of allulose from maltodextrin, a 0.20 mL reaction mixture containing 20 g/L maltodextrin, 50 mM phosphate buffered saline pH 7.2, 5 mM MgCl$_2$, 80 µM CoCl$_2$, 0.05 U of αGP, 0.05 U PGM, 0.05 U PGI, 0.05 U A6PE and 0.05 U A6PP is incubated at 50° C. for 24 hours. The reaction is stopped via filtration of enzyme with a Vivaspin 2 concentrator (10,000 MWCO). Allulose is detected and quantified using an Agilent 1100 series HPLC with refractive index detector and an Agilent Hi-Plex H-column. The mobile phase is 5 mM H$_2$SO$_4$, which runs at 0.6 mL/min. Standards of various concentrations of allulose are used to quantify our yield.

Example 10

A reaction mixture containing 200 g/L maltodextrin, 10 mM acetate buffer (pH 5.5), 5 mM MgCl2, 80 µM CoCl$_2$, and 0.1 g/L isoamylase is incubated at 80° C. for 24 hours. This is used to create another reaction mixture containing 20 g/L isoamylase treated maltodextrin, 50 mM phosphate buffered saline pH 7.2, 5 mM MgCl$_2$, 0.05 U of αGP, 0.05 U PGM, 0.05 U PGI, 0.05 U A6PE, and 0.05 U A6PP is incubated at 50° C. for 24 hours. Production of allulose is quantified as in Example 9.

Example 11

A reaction mixture containing 200 g/L maltodextrin, 10 mM acetate buffer (pH 4.5), 5 mM MgCl$_2$, and 1:200 dilution of Novozymes D6 pullulanase is incubated at 50° C. for 4 hours. This is used to create another reaction mixture containing 20 g/L pullulanase treated maltodextrin, 50 mM phosphate buffered saline pH 7.2, 5 mM MgCl$_2$, 80 µM CoCl$_2$, 0.05 U of αGP, 0.05 U PGM, 0.05 U PGI, 0.05 U A6PE, and 0.05 U A6PP is incubated at 50° C. for 24 hours. Production of allulose is quantified as in Example 9.

Example 12

To further increase allulose yields from maltodextrin, 0.05 U 4-glucan transferase (4GT) is added to the reaction described in example 9.

A 0.2 mL reaction mixture containing 20 g/L isoamylase treated maltodextrin (see example 9), 50 mM phosphate buffered saline pH 7.2, 5 mM MgCl2, 80 µM CoCl$_2$, 0.05 U of αGP, 0.05 U PGM, 0.05 U PGI, 0.05 U A6PE, 0.05 U A6PP, and 0.05 U 4GT is incubated at 50° C. for 24 hours. Production of allulose is quantified as in Example 9.

Example 13

To determine the concentration range of phosphate buffered saline (PBS), a 0.20 mL reaction mixture containing 50 g/L maltodextrin; 6.25 mM, 12.5 mM, 25 mM, 37.5 mM, or 50 mM phosphate buffered saline pH 7.2; 5 mM MgCl2; 0.1 U of aGP; 0.1 U PGM; and 0.1 U PGI is incubated at 50° C. for 6 hours. The short duration ensures completion is not reached, and therefore differences in efficiency can be clearly seen. Production of F6P is quantified using a fructose 6-phosphate kinase (F6PK)/pyruvate dehydrogenase (PK)/lactate dehydrogenase (LD) coupled enzyme assay where a decrease in absorbance at 340 nm indicates production of F6P. Respectively, a yield of 4.5 g/L, 5.1 g/L, 5.6 g/L, 4.8 g/L, or 4.9 g/L F6P is obtained for the reactions containing either 6.25 mM, 12.5 mM, 25 mM, 37.5 mM, or 50 mM phosphate buffered saline pH 7.2 (Table 1). These results indicate that a concentration of 25 mM PBS pH 7.2 is ideal for these particular reaction conditions. It is important to note that even the use of 6.25 mM PBS at pH 7.2 results in significant turnover due to phosphate recycling. This shows that the disclosed phosphate recycling methods are able to keep phosphate levels low even at industrial levels of volumetric productivity (e.g., 200-300 g/L maltodextrin).

TABLE 1

| Concentration of PBS pH 7.2 (mM) | g/L of F6P |
|---|---|
| 6.25 | 4.5 |
| 12.5 | 5.1 |
| 25 | 5.6 |
| 37.5 | 4.8 |
| 50 | 4.9 |

Example 14

To determine the pH range of the cascade reaction, a 0.20 mL reaction mixture containing 50 g/L maltodextrin; 50 mM phosphate buffered saline pH 6.0, 6.2, 6.4, 6.6, 6.8, 7.0 7.2, or 7.3; 5 mM MgCl2; 0.02 U of αGP; 0.02 U PGM; and 0.02 U PGI is incubated at 50° C. for 16 hours. The units are lowered to ensure completion is not reached, and therefore differences in efficiency can be clearly seen. Production of F6P is quantified as in example 12. Respectively, a yield of 4.0 g/L, 4.1 g/L 4.2 g/L, 4.1 g/L, 4.4 g/L, 4.1 g/L, 3.8 g/L or 4.0 g/L F6P was obtained for reactions containing 50 mM phosphate buffered saline at pH 6.0, 6.2, 6.4, 6.6, 6.8, 7.0, 7.2, or 7.3 (Table 2). These results indicate that a pH of 6.8 is ideal for these particular reaction conditions, although the system works through a wide pH range.

TABLE 2

| pH of PBS | g/L of F6P |
|---|---|
| 6.0 | 4.0 |
| 6.2 | 4.1 |
| 6.4 | 4.2 |
| 6.6 | 4.1 |
| 6.8 | 4.4 |
| 7.0 | 4.1 |
| 7.2 | 3.8 |
| 7.3 | 4.0 |

Example 15

To investigate scale-up, a 20 mL reaction mixture containing 50 g/L isoamylase treated maltodextrin (see Example 10), 50 mM phosphate buffered saline pH 7.2, 5 mM MgCl2, 80 µM CoCl$_2$, 10 U of αGP, 10 U PGM, 10 U PGI, 10 U A6PE, and 10 U A6PP is incubated at 50° C. for 24 hours. Production of allulose was quantified as in Example 9.

Example 16

To further increase allulose yields from maltodextrin, 0.05 U maltose phosphorylase is added to the reaction described in Example 9.

Example 17

To further increase allulose yields from maltodextrin, 0.05 U polyphosphate glucokinase and 75 mM polyphosphate is added to the reaction described in Example 9.

Example 18

To produce allulose from fructose, a reaction mixture containing 10 g/L fructose, 50 mM Tris buffer pH 7.0, 75 mM polyphosphate, 5 mM MgCl2, 80 μM CoCl$_2$, 0.05 U fructose polyphosphate kinase, 0.05 U A6PE, and 0.05 U A6PP is incubated at 50° C. for 24 hours. Production of allulose is quantified as in Example 9.

Example 19

To produce allulose from glucose, a reaction mixture containing 10 g/L glucose, 50 mM Tris buffer pH 7.0, 75 mM polyphosphate, 5 mM MgCl2, 80 μM CoCl$_2$, 0.05 U glucose polyphosphate kinase, 0.05 U PGI, 0.05 U A6PE, and 0.05 U A6PP is incubated at 50° C. for 24 hours. Production of allulose is quantified as in Example 9.

Example 20

To produce allulose from sucrose, a reaction mixture containing 10 g/L sucrose, 50 mM phosphate buffered saline pH 7.0, 5 mM MgCl2, 80 μM CoCl$_2$, 0.05 U sucrose phosphorylase, 0.05 PGM, 0.05 U PGI, 0.05 U A6PE, and 0.05 U A6PP is incubated at 50° C. for 24 hours. Production of allulose is quantified as in Example 9.

Example 21

To further increase yields of allulose from sucrose, 75 mM polyphosphate and 0.05 polyphosphate fructokinase is added to the reaction mixture in example 20. Production of allulose is quantified as in Example 9.

What is claimed is:

1. A process for preparing allulose, the process comprising:
   enzymatically converting fructose 6-phosphate (F6P) to allulose 6-phosphate (A6P); and
   enzymatically converting the A6P produced to the allulose.

2. The process of claim 1, further comprising enzymatically converting glucose 6-phosphate (G6P) to the F6P.

3. The process of claim 2, further comprising enzymatically converting glucose 1-phosphate (G1P) to the G6P.

4. The process of claim 3, further comprising enzymatically converting a saccharide to the G1P, wherein the saccharide is selected from the group consisting of a starch or a derivative thereof, cellulose or a derivative thereof and sucrose.

5. The process of claim 4, wherein the saccharide is the starch or the derivative of the starch selected from the group consisting of amylose, amylopectin, soluble starch, amylodextrin, maltodextrin, maltose, and glucose.

6. The process of claim 5, further comprising the step of converting the starch to the starch derivative, wherein the starch derivative is prepared by an enzymatic hydrolysis of the starch or by an acid hydrolysis of the starch.

7. The process of claim 1, wherein the process is conducted at a temperature ranging from 37° C. to 85° C., at a pH ranging from 5.0 to 8.0, and/or for 8 hours to 48 hours.

8. The process of claim 1, wherein the process is conducted in one bioreactor or in a plurality of bioreactors arranged in series.

* * * * *